United States Patent [19]

Burns et al.

[11] Patent Number: 4,966,458
[45] Date of Patent: Oct. 30, 1990

[54] OPTICAL SYSTEM FOR A MULTIDETECTOR ARRAY SPECTROGRAPH

[75] Inventors: Richard Burns, Webster; James Defendorf, Rochester; Edward King, Fairport; Cornelius McCarthy, Pittsford, all of N.Y.

[73] Assignee: Milton Roy Company, Peterburg, Fla.

[21] Appl. No.: 357,980

[22] Filed: May 26, 1989

Related U.S. Application Data

[63] Continuation-in-part of Ser. No. 191,262, May 6, 1988, Pat. No. 4,875,773.

[51] Int. Cl.⁵ ............................................. G01J 3/18
[52] U.S. Cl. ..................................... 356/328; 356/51
[58] Field of Search ............... 356/51, 303, 305, 319, 356/320, 323, 325, 326, 328, 332, 334

[56] References Cited

U.S. PATENT DOCUMENTS

| | | |
|---|---|---|
| 2,823,577 | 2/1958 | MacHler .............................. 356/303 |
| 3,279,308 | 10/1966 | Bartz et al. ............................. 356/51 |
| 3,519,816 | 7/1970 | Bartz et al. ............................. 356/51 |
| 3,554,649 | 1/1971 | Ridgway .............................. 356/334 |
| 4,022,531 | 5/1977 | Orazio et al. ......................... 356/332 |
| 4,562,585 | 1/1986 | Ward ................................... 356/320 |
| 4,781,456 | 11/1988 | Nogami .............................. 356/328 |

FOREIGN PATENT DOCUMENTS

| | | |
|---|---|---|
| 45898 | 2/1982 | European Pat. Off. ............ 356/320 |
| 111422 | 7/1982 | Japan ................................... 356/334 |
| 97039 | 6/1984 | Japan ................................... 356/306 |
| 7905871 | 2/1981 | Netherlands ........................ 356/320 |

OTHER PUBLICATIONS

Bausch & Lomb Catalog–Spectronic 600 Spectrophotometer, Nov. 7, 1968.

*Primary Examiner*—F. L. Evans

[57] ABSTRACT

An optical system for a multidetector array spectrophotometer which includes multiple light sources for emitting light of selected wavelength ranges and means for selectively transmitting the selected wavelength ranges of light to respective slits of a multi-slit spectrogrpah for multiple wavelength range detection. The spectrograph has two or more slits which direct the selected wavelength ranges of the light spectra to fall upon a dispersive and focusing system which collects light from each slit, disperses the light by wavelength and refocuses the light at the positions of a single set of detectors.

4 Claims, 3 Drawing Sheets

OPTICAL SYSTEM FOR A MULTIDETECTOR ARRAY SPECTROGRAPH

BACKGROUND OF THE INVENTION

This application is a continuation-in-part of application Ser. No. 191,262, filed May 6, 1988, now U.S. Pat. No. 4,875,773, entitled "NEW OPTICAL SYSTEM FOR A MULTIDETECTOR ARRAY SPECTROGRAPH".

FIELD OF THE INVENTION

This invention relates to an optical system for a multidetector array spectrograph to be used as a component of a spectrophotometer capable of measuring the absorbance of light by a sample as a function of the wavelength of light passing through the sample. This invention further relates to an optical system for a multidetector array spectrograph to be used as a component of a radiometer or emission spectrophotometer capable of measuring light energy emitted by a sample as a function of the wavelength of light. This invention further relates to an optical system for a multidetector array spectrograph to be used as a component of a reflectance spectrophotometer capable of measuring the reflectance of light from a sample as a function of light wavelength. This invention further relates to an optical system for a multidetector array spectrograph to be used as a component of an instrument capable of measuring the fluorescence or phosphorescence of a sample. This invention further relates to an optical system for a multidetector array spectrograph to be used as a component of an instrument capable of measuring the emission spectra or radiated energy of a sample as a function of wavelength.

DESCRIPTION OF THE PRIOR ART

For some years it has been known that meaningful laboratory analysis can be performed using instruments which measure the light absorbed by a sample, or reflected from a sample, or emitted from a sample as a function of wavelength. Spectrophotometers which measure the absorption characteristics of materials were produced by Bausch & Lomb in 1953. The absorption may be indicative of the presence of an impurity in a liquid under test, of solute in a solvent, of the color of the liquid, of the presence of solid matter suspended in the liquid, or the like. Numerous instruments for such applications are know. The art has well documented the wavelengths of light which are absorbed by various materials so that the absorption of light of a specific wavelength is indicative of the presence of a particular material in the sample under test. If the amount of incident light and transmitted light are compared, an indication of the amount of the absorptive material may be derived.

For these reasons, it is often desirable to make measurements of the amount of light that a sample absorbs as a function of the wavelength of light. It has also proven desirable to measure light absorption by a sample for selected ranges of wavelengths of light. Prior approaches to measuring light absorbed by a sample as a function of wavelength have typically utilized one or two very well known techniques.

One prior art technique is to generate white light and direct the generated white light into a monochromator. The monochromator receives white light emitted by the source and produces a monochromatic light of a selected wavelength by allowing only the small band of selected wavelengths to emerge from the exit slit of the monochromator. The light emerging from the monochromator travels through a sample under investigation. Typically, a portion of the light entering the sample would be absorbed by the sample itself. The remaining monochromatic light passing through the sample is measured by a single detector placed on the other side of the sample cell. In order to measure characteristics of the sample to absorb light over a range of wavelengths, the above experiment would be repeated for each wavelength in the selected range of wavelengths by adjusting the grating in the monochromator such that a next wavelength in the selected range would be emitted. Measurements would be repeated for each wavelength within the selected range. Such a procedure would successfully permit an examination of sample absorbency of light over a range of wavelengths. One such spectrophotometer has been marketed by the Milton Roy Company under the name "SPECTRONIC TM 2000". The primary disadvantage to devices which use such an approach is that when measurements of sample absorbency for a relatively large wavelength range is desired, the repeated adjustments to the monochromator would result in a relatively lengthy time to acquire data over the desired wavelength range.

The second technique is to measure sample absorption over wavelength ranges is to generate and transmit white light directly through the sample under investigation. Light passing through the sample is directed to a spectrograph where an array of photodetectors would simultaneously read the absorbency of the sample at a number of wavelengths simultaneously. In order to get high resolution of sample absorption readings over the large wavelength range typically present in such a method, various approaches have been taken.

One approach for measuring over a wide range of wavelengths is to use a detector array with a very large number of detecting elements in conjunction with a fixed grating and entrance slit. Unfortunately, such detector arrays tend to be very expensive, and therefore undesirable for many uses. Also, as detector arrays are planar, focus of the spectrum over the long array length is inherently poor.

Another approach includes the use of an array where the range of wavelengths studied could be changed by rotating the grating to a new location. This approach has proven undesirable as the mechanical system which positions the grating tends to adversely affect the accuracy of the device. Thus, to get repeatable results, the mechanical system which utilizes the reduced size detector array must be able to locate and position the grating with a high degree of precision. One such spectrophotometer has been marketed by Perkin-Elmer.

Yet another approach was to direct light from the entrance slit onto two or more gratings. Light from the gratings would be directed onto a corresponding sensor array. Such a system requires the proper alignment of numerous mechanical and optical components and proved too expensive for many spectrophotometric applications. One such spectrophotometer has been marketed by Hewlett Packard as their model 8450A spectrophotometer.

All of the above described techniques involve the use of a spectrograph where a single slit or aperture of various shapes is provided for light to pass through in combination with various dispersive and focusing systems for collecting light from the slit, dispersing the light by wavelength and refocusing at detectors. The limitation of the single slit designs described above is that resolution is limited by the number of detectors. It has proven difficult and expensive to obtain the electronics for a large number of detectors and to form an accurate high resolution image over the larger range of positions required for a large number of detectors.

Furthermore, if the detectors are small and close together, it may become optically difficult to disperse the wavelengths accurately without mixing in light from incorrect wavelengths. This is one source of stray light which is a type of error in dispersive instrumentation. Since gratings disperse light by means of interference effects, gratings image some light of wavelength lambda, one half lambda, one quarter lambda, etc., in the same place. When an instrument is designed such that the longest wavelength to be analyzed is more than twice the shortest wavelength to be analyzed and a grating is used as the dispersive element, then order filtering must be used to suppress the light from the half wavelength values which would normally reach the detector. For example, in a system designed to detect wavelengths from 400 to 900 nm, detectors between 800 and 900 nm would see some light from wavelengths between 400 and 450 nm. This problem is normally addressed by placing additional filters in the system which transmit light at a desired wavelength and absorb light at the half wavelength. Such filters may be inserted into the light path by moving mechanical means or may be inserted into the dispersive and focusing system to intercept light rays reaching the longer wavelength detectors only. These filters are generally called order sorting filters. If the additional filters are used improperly or scatter light within the dispersive and focusing system, then they become another source of stray light. If the wavelength range of the instrument is broad enough, it becomes difficult to fabricate optical elements which perform well over the total range of wavelengths, thus forcing the sacrificing of optimal performance in some areas to obtain acceptable performance over the complete range.

SUMMARY OF THE INVENTION

It is an object of this invention to provide an optical system for a multidetector array spectrograph included as a component of an optical system or instrument for the analysis of light energy as a function of wavelength where multiple slits are used in conjunction with a single fixed dispersive and focusing system and a collection of detectors at positions fixed with respect to the dispersive and focusing system.

It is another object of this invention to provide a multiple entrance slit spectrograph which achieves a multiple wavelength range without alignment errors, stray light sources and high cost associated with single slit, multiple wavelength detectors which rely upon moving parts to provide multiple wavelength capabilities.

It is still another object of this invention to use a single, fixed position grating to direct selected portions of the spectra onto a single medium resolution detector array.

Yet another object of this invention is to provide a low cost, easily focused, high resolution detector array which eliminates both the cost and complications of multiple grating systems.

Still yet another object of this invention is to provide a spectrograph where the use of multiple wavelength ranges dispersed on the same set of detectors improves the performance of the system by allowing the use of fewer detectors and smaller physical range of detector positions for the same resolution.

Yet another object of this invention is to provide a multiple wavelength range spectrograph which does not require movement of the optics, sensors, or dispersive elements to achieve switching between wavelength ranges.

Still yet another object of this invention is to provide a multidetector array spectrophotometer where experimental results may be easily repeated.

Yet another object of this invention is to reduce or eliminate the requirement for order sorting filters within the dispersive and focusing system while allowing for a total instrument wavelength range which exceeds a factor of two.

These and other objects and advantages are achieved by the present invention of an optical system for a multidetector array spectrophotometer which may include multiple light sources for emitting light of selected wavelength ranges and means for selectively transmitting the selected wavelength ranges of light to respective slits of a multi-slit spectrograph for multiple wavelength range detection. The spectrograph has two or more slits which direct the selected wavelength ranges of the light spectra to fall upon a dispersive and focusing system which collects light from each slit, disperses the light by wavelength and refocuses the light at the positions of a single set of detectors. Such a dispersive and focusing system may include a holographic concave grating which splits the wavelength range of emitted light falling upon the grating into its spectral components and directs the spectra to a fixed photodiode array.

BRIEF DESCRIPTION OF THE DRAWINGS

The invention may be better understood and further advantages and uses thereof are readily apparent, when considered in view of the following detailed description of the exemplary embodiments, taken together with the accompanying drawings in which:

FIG. 1 is a diagrammatic view of the new optical system for a multidetector array spectrophotometer of the present invention which illustrates the path of a first selected wavelength range of the light spectra; and.

DESCRIPTION OF THE PREFERRED EMBODIMENT

While the description of the preferred embodiment of the invention disclosed herein is a specific example where sample absorption characteristics are desired for two specific segments or wavelength ranges of the white light spectrum, it is entirely contemplated by the inventors that numerous modifications of the invention to allow the study of all segments of the light spectra or any number of selected wavelength ranges are possible by modifications of the types of light sources, filters or location and/or number of slits without departing substantially from the teachings of the invention as set forth below. In particular, it is contemplated that this invention shall be applied to instruments which evaluate energy distribution as a function of wavelength of light emitted from samples or sources and instruments which evaluate the energy distribution of light as a function of wavelength from samples in conjunction with other parameters of the sample such as position on the sample, temperature of the sample, time or other sample conditions.

Figure 1:
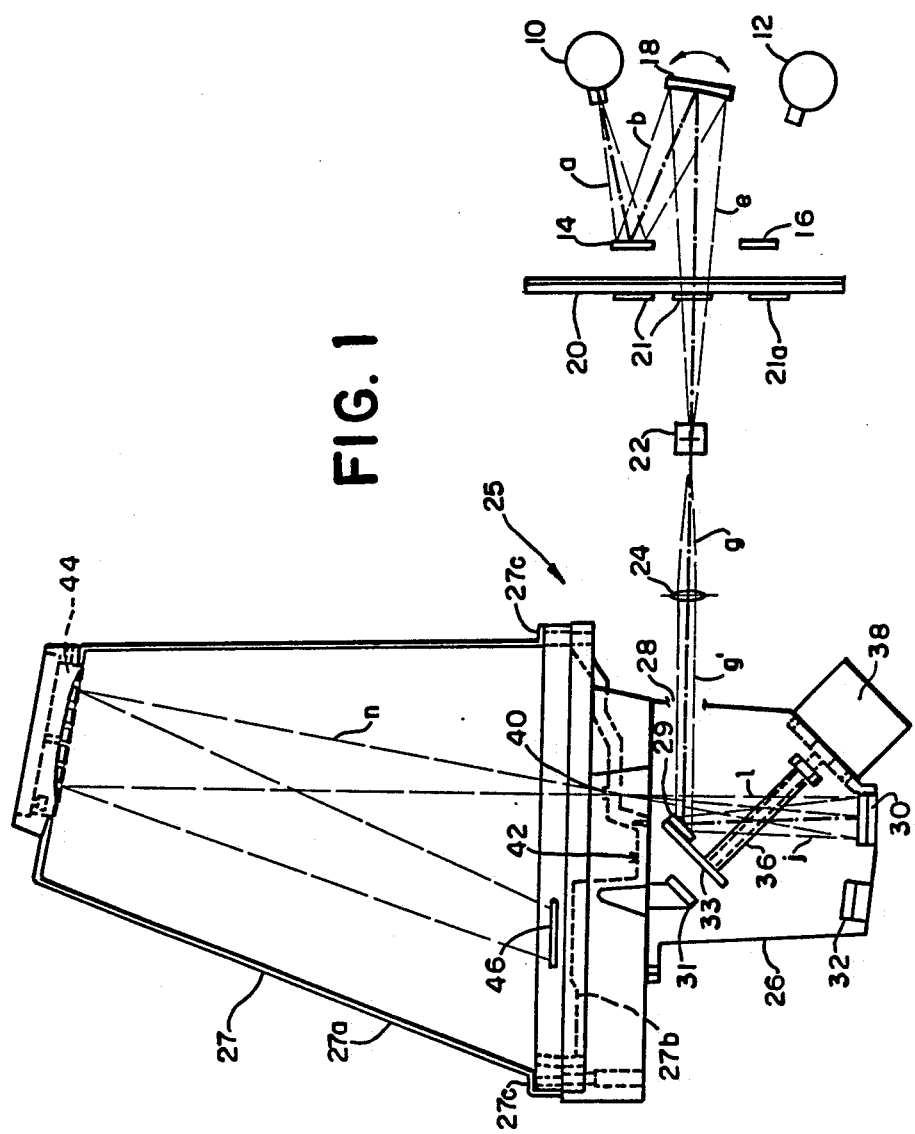
Figure 2:
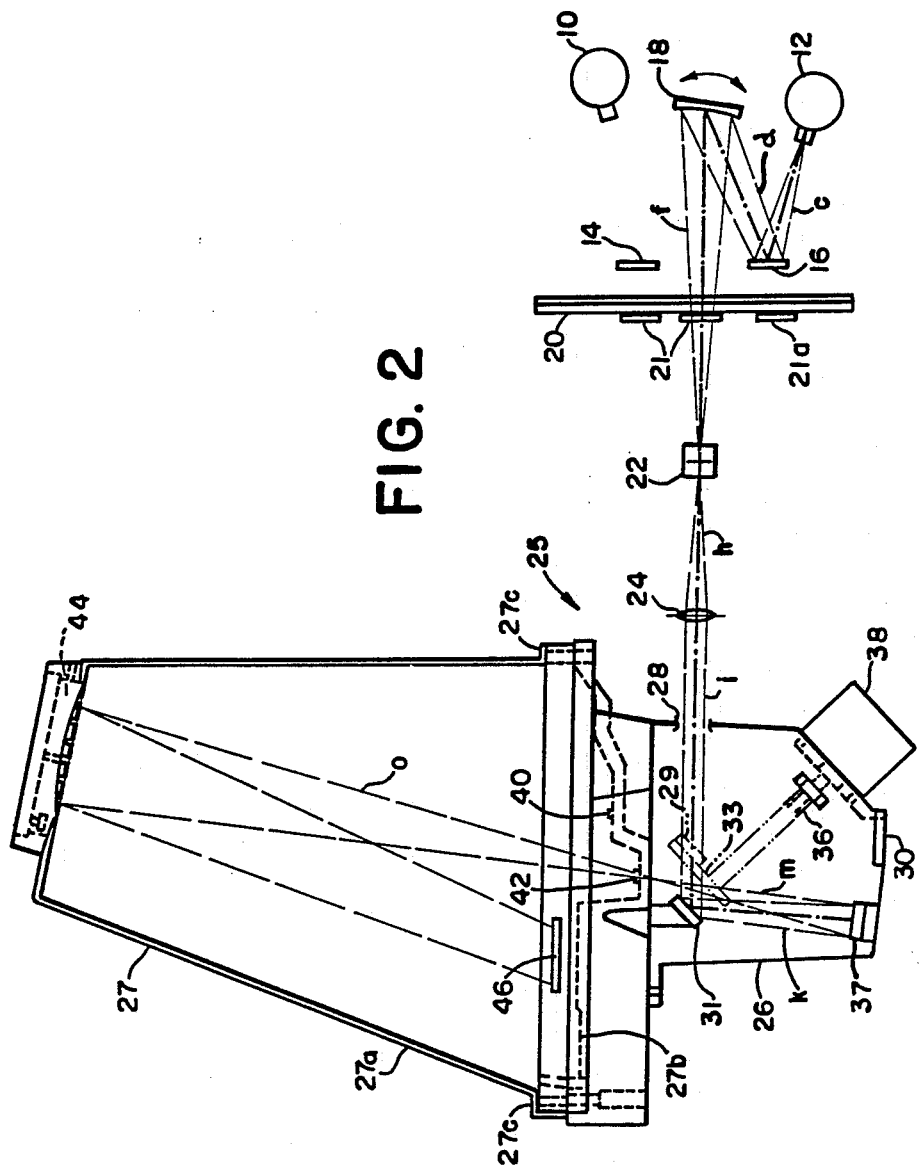
FIG. 2 is a diagrammatic view of the optical system of FIG. 1 which illustrates the path of a second selected wavelength range of the light spectra.

Turning first to FIG. 1, the present invention of a multi-wavelength range spectrophotometer includes means for generating plural wavelength ranges of light such as a light source 10 for emitting a first selected range of wavelengths and light source 12 for emitting a second selected range of wavelengths. For example, light source 10 may be a deuterium source for emitting light in the lower UV wavelength range of 190–545 nm and light source 12 may be a tungsten source for emitting light in the higher VIS (or visible) wavelength range of 545–900 nm. Light source 10 directs along line "a" toward mirror 14. Mirror 14 reflects the 190–545 nm wavelength light along line "b" towards focusing mirror 18. The orientation of focusing mirror 18 is controlled by a motor (not shown) such as a low power dc motor of conventional design in conjunction with the appropriate linkage (also not shown), which permits the rotation of focusing mirror 18 between two mechanical stops which determine first and second positions for mirror 18. In such a manner, mirror 18 is capable of selectively reflecting either light generated by source 10 or source 12. For example, in FIG. 1, focusing mirror 18 is shown in a first position which would direct light from source 10 and mirror 14 along path "e" while light from source 12 and mirror 16 would be directed along a path somewhere between mirror 14 and source 10. In such a manner, focusing mirror 18 is positioned to select light from source 10. By rotating mirror 18 approximately 15–20 degrees counterclockwise, mirror 18 will move to a second position as shown in FIG. 2 which will direct light from source 12 and mirror 16 along path "f" (see FIG. 2) and which will direct light from source 10 and mirror 14 somewhere between mirror 16 and source 12.

The operation of the spectrophotometer of the present invention when light source 10 is selected for reflection by the proper orientation of focusing mirror 18 shall now be described. Light originating from source 10 is reflected by focusing mirror 18 along line "e" where it passes through a rotatable filter wheel 20. Filter wheel 20 is rotatable by a motor (not shown) of conventional design such as a 1.8 degree stepper motor such that any one of a plurality of filters 21 may be selectively oriented with a high degree of precision so that light reflected by focusing mirror 18 will pass through the selected filter 21. In such a manner, filter 21 of filter wheel 20 may filter light wavelengths not part of the wavelength range under investigation from passing through sample compartment 22. Additional positions on the filter wheel may be used to modify the energy as a function of wavelength as emitted by the lamp to improve overall performance or to achieve specific functions such as wavelength alignment or protection of samples sensitive to specific wavelength ranges. In such a manner, filter wheel 20 provides light modifying means capable of optimizing the energy of light reaching the sample as a function of wavelength to match the wavelength range to be analyzed or to allow analysis of light from the sample as a function of the wavelength of light reaching the sample. Also, filter wheel 20 should include at least one filter position 21a where, if filter wheel 20 is rotated to that position, all light reflected by focusing mirror 18 will be blocked. Such a configuration is desirable when a dark reference is used or when no absorption measurements are being taken and it is desirable to keep light off the sample under investigation.

Light emitted by source 10 is directed by focusing mirror 18 along line "e" such that the light passes through filter 21 and sample compartment 22. Preferably, sample compartment 22, which contains a sample or component of which analysis is desired, is located such that the light reflected by focusing mirror 18 is focused at the location of sample compartment 22. In a typical experiment, the sample contained in sample compartment 22 may absorb at least part of the spectrum of light passing through the sample. It is the analysis of light which passes through the sample unabsorbed which is utilized for any one of the aforementioned methods of analyzing the sample.

Light passing through sample compartment 22 travels along line "g'" towards lens 24. Lens 24 directs light passing through sample compartment 22 on parallel paths along line "g'" towards mirror 29. Alternately, lens 24 may refocus light such that the beam emerging from it and reflected by mirrors 29 and 30 will be focused on slit 40, or if mirror 29 is not in this beam, be reflected by mirrors 31 and 32 and be focused on slit 42.

Spectrophotometer 25 comprises a first spectrophotometer compartment 26 and a second spectrophotometer compartment 27. Compartment 27 is formed by two castings attached together by conventional means. Casting 27a is mounted to casting 27b and the two are secured in a precise location with respect to each other by pins 27c. In such a manner, slit 40, slit 42 and detector means 46 such as a photodiode array 46, all of which are included as parts of compartment 27a and grating 44, which is mounted to casting 27b may be precisely located with respect to each other.

In such a manner, a multi-slit spectrograph wherein a single dispersive, focusing and detecting system such as a single grating and detector array may be used to analyze various selected wavelength ranges is provided. The division of the total instrument wavelength range into two or more ranges in a system which has no moving parts within the dispersive and focusing system may be sealed against air leaks and purged with a known gas or exposed to a drying agent allows for the development of high reliability measuring instruments which will operate over a wider range of environmental conditions than prior instruments. Further, the division of the total instrument range into two or more ranges by the use of multiple entrance slits allows the slits to be fabricated as an opaque layer on optical material which may be chosen to provide some or all of the order sorting filter required for the range of wavelengths to be analyzed when light passes through the particular entrance slit. Further, the division of the total instrument wavelength range into two or more ranges by the use of multiple entrance slits with particular optical elements associated with each slit allows the particular optical elements to be designed, constructed, and treated to optimize performance in the wavelength range particular to the wavelength range with which the optical elements are associated.

Again referring to FIG. 1, light re-directed either along a parallel path by lens 24 and travelling along line "g'" enters first spectrophotometer compartment 26 through an opening 28 sized to permit the entire beam of light emerging from lens 24 to enter first compartment 26. Generally speaking, first compartment 26 is intended to place a tangential image of the light entering through opening 28 onto one of two corresponding slits 40 or 42 as to be more fully described later. As such, the focal lengths, orientations and spacing of mirrors 29, 30, 31 and 32, which are mounted within compartment 26, are selected to achieve such a goal.

As mentioned, first spectrophotometer compartment 26 includes mirrors 29, 30, 31 and 32 for redirecting light entering compartment 26. Mirrors 30, 31 and 32 are fixedly mounted within compartment 26 using conventional means not shown in the drawings. Mirror 29 is mounted on conventional mounting means 33 which is attached via an arm 36 to a stepper motor 38 of conventional design capable of moving mounting means 33 via arm 36. Stepper motor 38 is thereby enabled to move mirror 29 into and out of the path of light entering compartment 26. For example, motor 38 may be a 1.8 degree stepper motor of conventional design capable of precisely repositioning mirror 29 out of the light path without any gear reductions.

When placement of mirror 29 in the path of light entering compartment 26 is desired, mirror 29 is placed in a first position in the plane of reflection such that all light entering compartment 26 will reflect off mirror 29 towards mirror 30. Fixed mirror 30 is positioned within compartment 26 such that all light reflected by mirror 29 will be reflected off mirror 30 as well. Fixed mirror 31 is positioned within compartment 26 such that when mirror 29 is moved to a second position out of the plane of reflection for the path of light entering compartment 28, all light entering compartment 26 will be reflected off mirror 31 towards mirror 32. Fixed mirror 32 is positioned within compartment 26 such that all light reflected by mirror 31 will be reflected off mirror 32 as well. In such a manner, positionable mirror 29 and fixed mirrors 30, 31 and 32 are configured to permit alternate reflection of entering light energy by mirrors 29 and 30 or by mirrors 31 and 32. By rotating mirror 29 in its plane of reflection into or out of the path of the light from lens 24, the position of mirror 29 selects slit 40 or 42. Because the plane of rotation is the plane of reflection, precise positioning of the mirror is not required and stepping errors do not affect the angles of rays reflecting from the mirror.

It is further contemplated that in the embodiment of the invention where multiple slits are utilized in conjunction with multiple generated wavelength ranges of light, mirror 29 may be replaced with a plurality of mirrors in multiple parallel planes. In this embodiment, the plurality of mirrors may intercept and reflect light entering compartment 28 such that the entering light corresponding to a multiple number of wavelength ranges may be selectively directed to a corresponding one of an equal number of entry ports or slits provided as part of the spectrograph of the present invention.

As previously noted, the operation of the optical system for the spectrophotometer of the present invention is presently being described for the case where light in the UV wavelength range of 190-545 nm emitted from light source 10 has been selected to pass through sample compartment 22 and into compartment 26. For this particular example, when light emitted by source 10 is selected to enter compartment 26, mirror 29 is positioned in the plane of reflection of the path of light entering compartment 26 and will reflect the incoming light energy along path "j" towards fixed mirror 30. Fixed mirror 30 reflects the light energy again such that the light will travel along path "1" and towards slit 40. Since mirrors 29 and 30 are associated with slit 40 and are intended to pass UV light, mirrors 29 and 30 may be optimized for UV imaging and energy transfer while suppressing non UV energy performance by proper design and coating.

The interface between compartments 26 and 27 includes first entry port or slit 40 and second entry port or slit 42. Preferably, slits 40 and 42 are spaced apart such that light reflected off mirror 30 converges at slit 40 and light reflected off mirror 32 converges at slit 42. In the specific embodiment disclosed, the desired result is achieved by spacing slits 40 and 42 slightly apart and placing mirror 30 slightly further away from its corresponding slit 40. In such a manner, when light passes through slit 42, the second selected wavelength range (here, the higher VIS light wavelengths of the spectra) under investigation will be detected by array detector 46, and when light passes through slit 40, the first selected wavelength range (here, the lower wavelengths UV spectra) under investigation will fall upon the same array detector. In such a manner, a multi-slit spectrograph wherein a single dispersive, focusing and detecting system such as a single grating and detector array may be used to analyze various selected wavelength ranges.

To achieve such an effect, slits 40 and 42 are different both in angle with respect to the grating 44 and detector 46 and in distance from grating 44 in order to optimize focus for the selected wavelengths ranges of the spectrum under investigation. It should be clearly noted, however, that the specific orientation of slits 40 and 42 with respect to each other may be varied depending on the selected wavelength ranges or the orientation of reflecting mirrors 29, 30, 31 and 32 and the present invention should not be restricted to any specific slit orientation.

Light of the first selected wavelength which passes through slit 40, enters compartment 27 and travels along path "n" where it is dispersed by wavelength and re-focused by holographic grating 44, which is fixed to second spectrophotometer compartment 27 by conventional means, to a photodiode array 46 such as a linear 1024 element photodiode array. The photodiode array may be any one of numerous types available in the marketplace. The desired dispersion in the UV range determines the angle from the center of the grating to UV slit 40 and the distance between grating 44 and slit 40 is chosen for best focus on photodiode array 46. UV slit 40 is fabricated by photoetching chrome on a piece of quartz. Since the wavelength range falling on the detector when light passes through slit 40 is intended to be in the UV range, the physical material of this slit may be selected to transmit UV wavelengths while suppressing wavelengths not detected when this slit is in use. This selection of slit material and fabrication further improves system performance by decreasing error due to light at incorrect wavelengths.

The orientation of focusing mirror 18 is controlled by a motor (not shown) which, in conjunction with the appropriate linkage (also not shown), may be rotated such that the mirror 18 is capable of selectively reflecting either light generated by source 10 or source 12.

Turning next to FIG. 2, the operation of the spectrophotometer of the present invention when light source 12 is selected for generating a second selected wavelength range (here, a tungsten source of wavelength range of 545-900 nm) when sample absorption studies for the second wavelength range is desired. Light emitted by source 12 is directed along line "c" towards reflecting mirror 16. Mirror 16 reflects the 545-900 nm wavelength light along line "d" towards focusing mirror 18. Focusing mirror 18, which has been repositioned by the aforementioned motor such that mirror 18 will reflect light transmitted by source 12 only, reflects light transmitted by mirror 16 along line "f" where it passes through rotatable filter wheel 20. Prior to repositioning focusing mirror 18 to transmit light from source 12, filter wheel 20 should be rotated to a next position so that a next filter 21 better capable of filtering stray light not part of the second wavelength range under investigation will be positioned in the path of light being emitted by source 12.

Light emitted by source 12 is directed by focusing mirror 18 along line "f" such that the light passes through next filter 21 and sample compartment 22 containing the sample previously analyzed for the wavelength range emitted by source 10. Again, the sample contained in sample compartment 22 may absorb a part of the spectrum of the light passing through the sample. Light passing through sample compartment 22 travels along line "h" towards lens 24.

Lens 24 re-directs light passing through sample compartment 22 along a parallel path along line "i" towards mirror 31. Alternately lines 24 may be a focusing lens which would instead re-focus light passing through sample compartment 22 into a converging beam of light such that light emerging from lens 24 will be focused at a point within spectrophotometer 26 and before mirror 31. Light re-directed along parallel paths by lens 24 and travelling along line "i" enters first spectrophotometer compartment 26 through an opening 28 sized to permit the entire beam of light emerging from lens 24 to enter first compartment 26.

So that the second wavelength range, i.e. light emitted by source 12, will pass through slit 42 instead of slit 40, mirror 29 is moved to the previously disclosed second position located out of the path of light entering first compartment 26 through opening 27 prior to the emission of light by source 12. In such a manner, all light entering compartment 26 which originated from source 12 will be reflected off mirror 31 towards mirror 32.

Mirror 31 will thereby reflect light entering compartment 26 along path "k" towards fixed mirror 32. Fixed mirror 32 reflects the light energy again such that the light will travel along path "m" and towards slit 42. Since mirrors 31 and 32 are associated with slit 42 and are intended to pass visible light, mirrors 31 and 32 may be optimized for visible light imaging and energy transfer while suppressing energy transfer in other wavelength ranges by proper design and coating. Light passing through slit 42 enters spectrophotometer compartment 27, travels long path "o" and is dispersed by wavelength and refocused by holographic grating 44 onto photodiode array 46. Here, the desired dispersion in the visible range determines the angle from the center of the grating to visible slit 42 and the distance between grating 44 and slit 42 is chosen for best focus on detector array 46. Since the wavelengths of light reaching the detector when light passes through slit 42 are intended to be in the visible range, slit 42 may be constructed by photoetching chrome on a piece of optical material chosen to suppress wavelengths outside this range, thus improving system performance by decreasing error due to light at incorrect wavelengths reaching the detector.

The preferred embodiment of the relative positions of port 40, port 42, grating 44, and detector 46 may be further described by defining the angles between the grating and the ports and between the grating and the detector. This is shown in FIG. 3.

Figure 3:
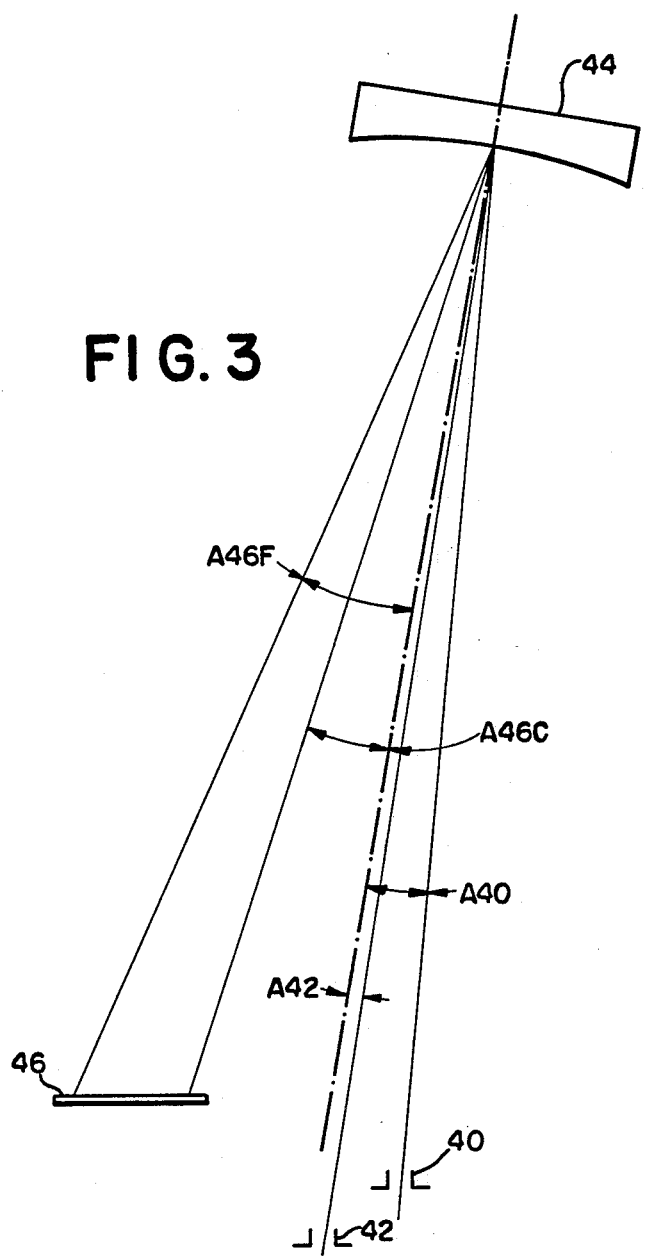
FIG. 3 is an enlarged diagrammatic view useful to explain and define the relative positions of various elements, together with the angles between such various elements, of the optical system in accordance with the invention.

It is the nature of a grating to disperse light by wavelength in a preferred plane. FIGS. 1, 2, and 3 are drawn such that this plane is the plane of the paper. This discussion refers to angles in this preferred plane or projected onto this plane. To make this description clear, we first define a line normal to the surface of the grating at the center of the grating to be the grating normal. For purposes of this discussion, this is a convention used to simplify the description of the relative positions of these components. Then, using the chosen grating normal, we may define angles from the grating normal as rotation about the point at the intersection of the grating normal and the grating surface. That is, the concave grating 44 has a preferred plane to disperse light and the concave grating 44 has a normal lying in the preferred plane relative to which angles may be defined as rotations around a rotation point located at the intersection of the grating normal and the surface of the grating. Using the convention that clockwise rotation corresponds to positive angles, the preferred embodiment would be further described as follows:

The angle from grating normal to the center of the port 40, labeled A40 on FIG. 3, is in the range between −5.2 and −5.4 degrees and optimal at −5.336 degrees.

The angle from grating normal to the center of the port 42, labeled A42 on FIG. 3, is in the range between −0.3 and −0.5 degrees and optimal at −0.421 degrees.

The angle from grating normal to closest sensor position or element on detector 46, labeled A46C on FIG. 3, is more positive than 8.3 degrees and optimal for the 190 and 545 nm wavelengths at 8.437 degrees.

The angle from grating normal to farthest sensor position or element on detector 46, labeled A46F on FIG. 3, is more negative than 14.4 degrees, i.e. is rotated counterclockwise from 14.4 degrees, and optimal for 545 and 900 nm wavelengths at 14.304 degrees.

It should be clear that by choosing the convention that counterclockwise rotation corresponds to positive angles, the same embodiment would be described with all signs reversed.

It should also be clear that other variations in the convention for defining the grating normal are possible which lead to the same embodiment. In particular, the grating normal could be defined as a line normal to the grating surface from a point chosen on the grating surface such that the dispersion of light by the grating is symmetrical about the normal so defined.

It should also be clear that other port positions between −0.3 degrees from the grating normal and −5.4 degrees from the grating normal can be chosen to replace either port 40 or port 42 or as additional port positions.

In accordance with the invention, the positions or locations of the light entry ports relative to the concave grating 44 are chosen so as to effect optimum focus of the light entering at the ports at the detector means 46. As for example, with center of the first port 40 being chosen to be at a specific angle chosen to be between −0.3 and −5.4 degrees from the grating normal, the location of port 40 along a line defined by the chosen angle and the rotation point (located at the intersection of the grating normal and the surface of the grating) is selected so as to obtain optimum focus of light entering the port 40 at the detector means 46 by the grating 44. Likewise for port 42, with the center of the second port 42 being chosen to be at a specific angle chosen to be between −0.3 and −5.4 degrees from the grating normal, the location of port 42 along a line defined by the chosen angle and the rotation point is selected so as to obtain optimum focus of light entering the port 42 at the detector means 46 by the grating 44. Of course, the same method would be used to locate any additional light entry ports so as to effect optimum focus of light by the grating 44 at the detector means 46.

Thus, there has been described herein, apparatus for a new optical system for a multidetector array spectrograph which provides a multi-slit configuration which permits the use of a single dispersing and focusing system such as fixed grating and a single photodiode linear array detector for recording multiple wavelength ranges such as a high light wavelength range and a low light wavelength range which are both passed through a sample. However, those skilled in the art will recognize that many modifications and variations may be made in the techniques described herein without departing substantially from the concept of the present invention. Accordingly, it should be clearly understood the form of the invention described herein is exemplary only and is not intended as a limitation upon the scope of the present invention.

I claim:

1. An apparatus for the measurement of light intensity by wavelength comprising:
   a concave grating for the dispersion and focusing of light by wavelength; said concave grating having a preferred plane to disperse light and having a normal lying in said preferred plane relative to which angles may be defined as rotations around a rotation point located at the intersection of said normal and the surface of said grating,
   detector means optically coupled to said concave grating for the conversion of light energy to electrical energy indicative of said light intensity; said detector means comprising a plurality of light sensitive elements, said detector means being positioned such that said light sensitive elements are present at or between angles of 8.3 and 14.4 degrees from the grating normal,
   a first port for entrance of light to the apparatus; the center of said first port being at a specific first angle chosen to be between −0.3 and −5.4 degrees from the grating normal, the location of said first port along a line defined by said chosen first angle and said rotation point selected so as to obtain optimum focus of light entering at said first port at said detector means by said grating, and
   a second port for entrance of light to the apparatus; the center of said second port being at a specific second angle chosen to be between −0.3 and −5.4 degrees from the grating normal, the location of said second port along a line defined by said chosen second angle and said rotation point selected so as to obtain optimum focus of light entering at said second port at said detector means by said grating.

2. Apparatus according to claim 1 wherein
   said first chosen angle for said first port is between −5.2 and −5.4 degrees from the grating normal, and
   said second chosen angle for said second port is between −0.3 and −0.5 degrees from the grating normal.

3. Apparatus according to claim 2 wherein
   said first chosen angle is −5.336 degrees from the grating normal, and
   said second chosen angle is −0.421 degrees from the grating normal.

4. Apparatus according to claim 1 further comprising at least one additional port for entrance of light to the apparatus; the center of said one additional port being at a specific additional angle chosen to be between −0.3 and −0.54 degrees from the grating normal, the location of said additional port along a line defined by said chosen additional angle and said rotation point selected so as to obtain optimum focus of light entering at said additional port at said detector means by said grating.

* * * * *